(12) United States Patent
Bok et al.

(10) Patent No.: US 6,455,577 B2
(45) Date of Patent: Sep. 24, 2002

(54) FLAVANONE DERIVATIVES AND COMPOSITION FOR PREVENTING OR TREATING BLOOD LIPID LEVEL-RELATED DISEASES COMPRISING SAME

(75) Inventors: Song-Hae Bok; Tae-Sook Jeong; Sang-Ku Lee, all of Daejeon; Ju-Ryong Kim, Kwangju; Surk-Sik Moon, Daejeon; Myung-Sook Choi, Daegu; Byung-Hwa Hyun, Daejeon; Chul-Ho Lee, Daejeon; Yang-Kyu Choi, Daejeon, all of (KR)

(73) Assignee: Korea Research Institute of Bioscience and Biotechnology, Daejon (KR)

( * ) Notice: Subject to any disclaimer, the term of this patent is extended or adjusted under 35 U.S.C. 154(b) by 0 days.

(21) Appl. No.: 09/768,740

(22) Filed: Jan. 24, 2001

(30) Foreign Application Priority Data

Dec. 30, 2000 (KR) .......................... 2000-87185

(51) Int. Cl.[7] .............................................. A61K 31/35
(52) U.S. Cl. ...................................... 514/456; 549/403
(58) Field of Search ........................... 549/403; 514/456

(56) References Cited

PUBLICATIONS

Krishnamurty, et. al., "On the first one–pot general synthesis of novel 3–benzal–2,3–dihydro–4H–[1]benzopyran–4–ones" CA 112:98248 (1990).*

* cited by examiner

Primary Examiner—Amelia Owens

(74) Attorney, Agent, or Firm—Katten Muchin Zavis Rosenman

(57) ABSTRACT

A compound of formula (I) treating or preventing an elevated blood lipid level-related disease and inhibiting the activities of acyl-CoA:cholesterol-O-acyltransferase (ACAT) and 3-hydroxy-3-methylglutaryl CoA(HMG-CoA) reductase:

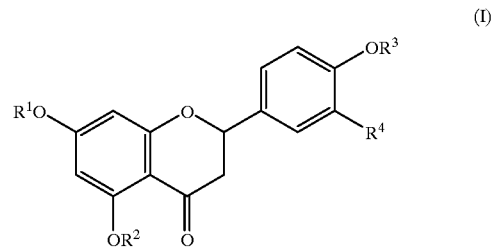

(I)

wherein, $R^1$ is $R^5 R^6 CO$ group;

$R^2$ is H or $R^6 CO$ group;

$R^3$ is H, CH3, $R^5$ or $R^6 CO$ group;

$R^4$ is H, OH, $OR^5$ or $R^6 COO$ group;

$R^5$ is a $C_{2-5}$ alkyl group substituted with a phenyl group optionally having one or more substituents selected from the group consisting of $C_{1-3}$ alkyl, OH, Cl and $NO_2$; a $C_{1-5}$ alkyl group substituted with a naphthyl group optionally having one or more substituents selected from the group consisting of $C_{1-3}$ alkyl, OH, Cl and $NO_2$; a $C_{10-18}$ alkyl; or a $C_{10-18}$ alkenyl group; and $R^6$ is a $C_{10-18}$ alkenyl group; or an aryl group optionally having one or more substituents selected from the group consisting of $C_{1-3}$ alkyl, OH, Cl or $NO_2$.

20 Claims, 6 Drawing Sheets

FLAVANONE DERIVATIVES AND COMPOSITION FOR PREVENTING OR TREATING BLOOD LIPID LEVEL-RELATED DISEASES COMPRISING SAME

FIELD OF THE INVENTION

The present invention relates to novel flavanone derivatives; a process for preparing same; a pharmaceutical composition containing same for treating or preventing an elevated blood lipid level-related disease, inhibiting the activity of acyl-CoA:cholesterol-O-acyltransferase(ACAT) and inhibiting the activity of 3-hydroxy-3-methylglutaryl CoA(HMG-CoA) reductase.

BACKGROUND OF THE INVENTION

In recent years, coronary artery diseases, e.g., atherosclerosis and hypercholesterolemia, have increasingly become a major cause of deaths. It has been reported that an elevated plasma cholesterol level causes the deposition of fat, macrophages and foam cells on the wall of blood vessels, such deposit leading to plaque formation and then to atherosclerosis(Ross, R., *Nature,* 362, 801–809(1993)). One of the methods for decreasing the plasma cholesterol level is alimentotherapy to reduce the ingestion of cholesterol and lipids. Another method is to inhibit the absorption of cholesterol by inhibiting enzymes involved therein.

Acyl-CoA:cholesterol-O-acyltransferase(ACAT) promotes the esterification of cholesterol in blood. Foam cells are formed by the action of ACAT and contain a large amount of cholesterol ester carried by low density lipoproteins. The formation of foam cells on the wall of artery increases with the ACAT activity, and, accordingly, an inhibitor of ACAT may also be an agent for preventing atherosclerosis. Further, it has been reported that the blood level of LDL-cholesterol can be reduced by inhibiting the ACAT activity(Witiak, D. T. and D. R. Feller(eds.), *Anti-Lipidemic Drugs: Medicinal, Chemical and Biochemical Aspects*, Elsevier, pp159–195(1991)).

Therefore, numerous efforts have been made to develop medicines which inhibit ACAT activity; and, as a result, several compounds isolated from the cultures of various microorganisms have been reported. Examples of such compounds include pyripyropenes isolated from the culture of Aspergillus fumigatus(S. Omura et al., *J. Antibiotics,* 46, 1168–1169(1993)) and Acaterin isolated from Pseudomonas sp.(S. Nagamura et al., *J. Antibiotics,* 45, 1216–1221 (1992)).

Further, it has been reported that hypercholesterolemia can be treated effectively by reducing the rate of cholesterol biosynthesis through the inhibition of HMG-CoA reductase which mediates the synthesis of mevalonic acid, an intermediate in a biosynthesis of sterol or isoprenoids (*Cardiovascular Pharmacology*, William W. Parmley and Kanu Chatterjee Ed, Wolf Publishing, pp8.6–8.7, 1994).

Accordingly, numerous efforts have been made to develop medicines to inhibit HMG-CoA reductase; and, as a result, several compounds derived from *Penicillium* sp. and *Aspergillus* sp. have been commercialized. Specifically, Lovastatin® and Simvastatin® developed Merck Co., U.S.A., and Pravastatin® developed by Sankyo Co., Japan, have been commercialized(C. D. R. Dunn, *Stroke: Trends, Treatment and Markets*, SCRIPT Report, PJB Publications Ltd., 1995). However, these medicines are very expensive and a long-term administration thereof is known to induce an adverse side effect of increasing creatine kinase in the liver. Accordingly, there has continued to exist a need to develop an inexpensive and non-toxic inhibitor of HMG-CoA reductase.

On the other hand, deterioration of hepatic functions may occur due to an excessive intake of alcohol or foods having a high lipid content, or an infection of hepatitis B or C virus, and it may develop into hepatitis, hepatocirrhosis or hepatic cancer. In particular, the excessive intake of fat-containing foods and alcohol causes fatty liver wherein a large amount of lipids is deposited in the liver tissue and the levels of serum GOT(glutamate-oxaloacetate transaminase), GPT (glutamate-pyruvate transaminase) and γ-GTP(γ-glutamyl transpeptidase) are elevated(T. Banciu et al., *Med. Interne.,* 20, 69–71(1982); and A. Par et al., *Acta. Med. Acad. Sci. Hung.,* 33, 309–319(1976)). Accordingly, there has continued to exist a need to develop non-toxic agents for preventing and treating elevated blood lipid level-related diseases, and hepatic diseases.

The present inventors have reported that naringenin and hesperetin, which are the aglycons of naringin and hesperidin found in lemons, grapefruits, tangerines and oranges (Citrus sinensis), have activities for inhibiting hyperlipidemia and atherosclerosis (U.S. Pat. Nos. 5,877,208 and 5,763,414).

The present inventors have continued to screen compounds having the flavanone core structure; and have discovered that certain novel flavanone derivatives have enhanced activity in treating or preventing elevated blood lipid level-related diseases, inhibiting an activity of acyl-CoA:cholesterol-O-acyltransferase(ACAT) and inhibiting an activity of 3-hydroxy-3-methylglutaryl CoA(HMG-CoA) reductase.

SUMMARY OF THE INVENTION

Accordingly, it is an object of the present invention to provide novel flavanone derivatives.

It is another object of the present invention to provide a process for the preparation of the inventive flavanone derivatives.

It is a further object of the present invention to provide a pharmaceutical composition for treating or preventing an elevated blood lipid level-related disease, inhibiting an activity of acyl-CoA:cholesterol-O-acyltransferase(ACAT) and inhibiting an activity of 3-hydroxy-3-methylglutaryl CoA(HMG-CoA) reductase.

It is a further object of the present invention to provide a method for treating or preventing an elevated blood lipid level-related disease, inhibiting an activity of acyl-CoA:cholesterol-O-acyltransferase(ACAT) and inhibiting an activity of 3-hydroxy-3-methylglutaryl CoA(HMG-CoA) In accordance with the present invention, there is provided a novel compound of formula (I):

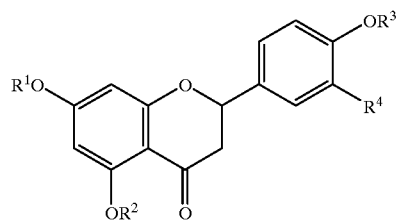

wherein,
$R^1$ is $R^5$ or $R^6CO$ group;
$R^2$ is H or $R^6CO$ group;

$R^3$ is H, CH3, $R^5$ or $R^6CO$ group;

$R^4$ is H, OH, $OR^5$ or $R^6COO$ group;

$R^5$ is a $C_{2-5}$ alkyl group substituted with a phenyl group optionally having one or more substituents selected from the group consisting of $C_{1-3}$ alkyl, OH, Cl and $NO_2$; a $C_{1-5}$ alkyl group substituted with a naphthyl group optionally having one or more substituents selected from the group consisting of $C_{1-3}$ alkyl, OH, Cl and $NO_2$; a $C_{10-18}$ alkyl; or a $C_{10-18}$ alkenyl group; and $R^6$ is a $C_{10-18}$ alkenyl group; or an aryl group optionally having one or more substituents selected from the group consisting of $C_{1-3}$ alkyl, OH, Cl or $NO_2$.

BRIEF DESCRIPTION OF THE DRAWINGS

The above and other objects and features of the present invention will become apparent from the following description of the invention, when taken in conjunction with the accompanying drawings, in which.

DETAILED DESCRIPTION OF THE INVENTION

Figure 1A:
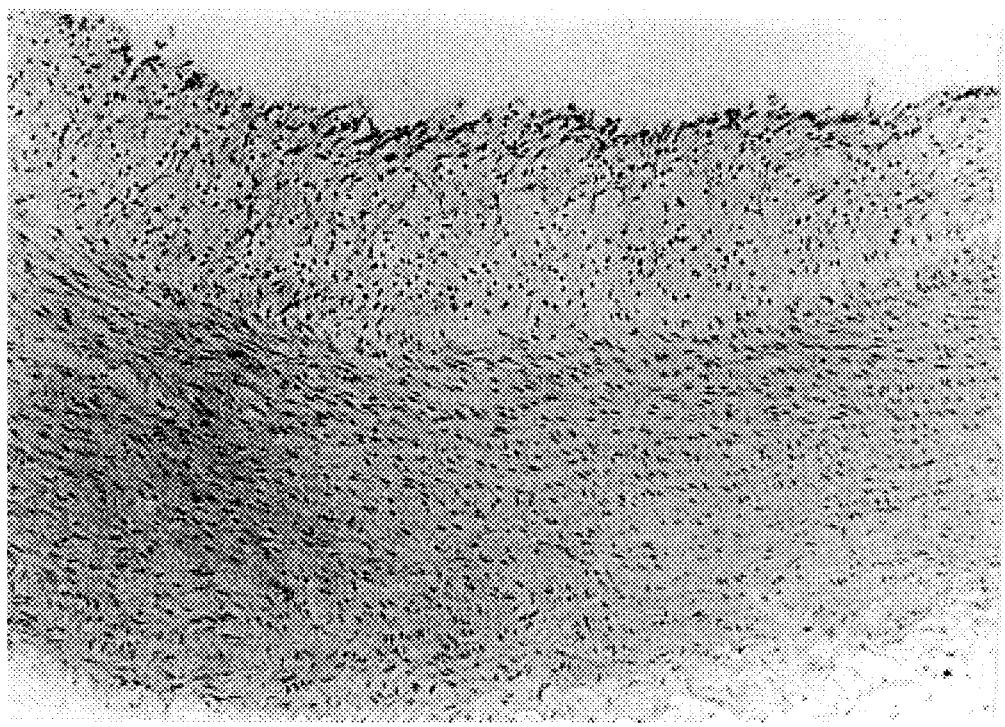
FIGS. 1A, 1B and 1C show the arteries of the rabbits administered with 1% cholesterol(control); 1% cholesterol plus 1 mg/kg Lovastatin®; and 1% cholesterol plus 0.1% NG5006(compound 4), respectively.

Among the compounds of the present invention, the preferred are those wherein $R^1$ is phenethyl, cetyl, stearyl, $CH_2=CH(CH_2)_9$—, 1-naphthalenemethyl, oleoyl, linoleoyl, benzoyl, o-chlorobenzoyl, p-chlorobenzoyl, o-methoxybenzoyl, p-methoxybenzoyl or 1-naphthoyl; $R^2$ is H, oleoyl, benzoyl, o-chlorobenzoyl, p-chlorobenzoyl, o-methoxybenzoyl, p-methoxybenzoyl or 1-naphthoyl; and $R^3$ is H, $CH_3$, phenethyl, cetyl, stearyl, oleoyl, benzoyl, o-chlorobenzoyl, p-chlorobenzoyl, o-methoxybenzoyl, p-methoxybenzoyl or 1-naphthoyl; and $R^4$ is H, OH or O-oleoyl.

More preferred are compounds of formula (I) having $R^1$, $R^2$, $R^3$ and $R^4$ groups shown in Table I:

TABLE I

| No. | $R^1$ | $R^2$ | $R^3$ | $R^4$ |
|---|---|---|---|---|
| 1 | phenethyl | H | H | H |
| 2 | phenethyl | H | phenethyl | H |
| 3 | phenethyl | H | $CH_3$ | OH |
| 4 | cetyl | H | H | H |
| 5 | cetyl | H | $CH_3$ | OH |
| 6 | cetyl | H | cetyl | H |
| 7 | stearyl | H | H | H |
| 8 | stearyl | H | stearyl | H |
| 9 | stearyl | H | $CH_3$ | OH |
| 10 | $CH_2CH(CH_2)_9$ | H | H | H |
| 11 | 1-naphthalenemethyl | H | H | H |
| 12 | oleoyl | H | H | H |
| 13 | oleoyl | H | oleoyl | H |
| 14 | oleoyl | oleoyl | oleoyl | H |
| 15 | oleoyl | H | $CH_3$ | OH |
| 16 | oleoyl | H | $CH_3$ | O-oleoyl |
| 17 | linoleoyl | H | H | H |
| 18 | benzoyl | H | H | H |
| 19 | benzoyl | H | $CH_3$ | OH |
| 20 | benzoyl | benzoyl | benzoyl | H |
| 21 | p-chlorobenzoyl | p-chlorobenzoyl | p-chlorobenzoyl | H |
| 22 | o-chlorobenzoyl | o-chlorobenzoyl | o-chlorobenzoyl | H |
| 23 | o-methoxybenzoyl | o-methoxybenzoyl | o-methoxybenzoyl | H |
| 24 | p-methoxybenzoyl | p-methoxybenzoyl | p-methoxybenzoyl | H |
| 25 | 1-naphthoyl | H | H | H |
| 26 | 1-naphthoyl | H | $CH_3$ | OH |
| 27 | 1-naphthoyl | 1-naphthoyl | 1-naphthoyl | H |

Most preferred compound of the inventive compounds is naringenin 7-O-cetyl ether.

Ether-type flavanone derivatives of the inventive compounds may be prepared by a process which comprises dissolving naringenin or hesperetin in an organic solvent; adding 1 to 1.5 equivalents of an alkyl halide such as hexadecanyl bromide or octadecanyl bromide and 1 to 3 equivalents of a base such as sodium carbonate to the solution obtained above; and stirring the mixture at a temperature ranging from 60 to 90° C. for 3 to 20 hours.

Exemplary organic solvents that may be used in the present may include dimethylformamide(DMF), dimethylsulfoxide(DMSO), tetrahydrofuran(THF), acetone and a mixture thereof.

After the reaction, the resulting solution is diluted with ethylacetate(EtOAc) and washed with water to remove the organic solvent. The resulting solution is washed with physical saline water and dried, filtered and the filtrate is concentrated to obtain an ether-type flavanone derivative.

Further, ester-type flavanone derivatives of the inventive compounds may be prepared by the conventional method. For example, naringenin or hesperetin is dissolved in an organic solvent such as tetrahydrofuran(THF) and dichloromethane($CH_2Cl_2$) and 1 to 10 equivalents of triethylamine($Et_3N$) is added thereto. The mixture is cooled with ice water and 1 to 10 equivalents of acyl chloride is added thereto and then, reacted for 2 to 10 hours. The acyl chloride which may be used in the above reaction is oleoyl chloride, benzoyl chloride, p-chlorobenzoyl chloride, o-chlorobenzoyl chloride, p-methoxybenzoyl chloride, o-methoxybenzoyl chloride or 1-naphthoyl chloride. The resulting solution is diluted with ethylacetate(EtOAc), followed by washing with saturated sodium hydrogen carbonate solution and saline water. The resulting extract is dried, filtered and the filtrate is concentrated to obtain an ester-type flavanone derivative. Further, the compound of the present invention may be purified by triturating with an insoluble solvent or subjecting to chromatography such as silica gel chromatography and C-18 HPLC.

The flavanone derivatives of the present invention exert inhibitory effects on: elevated blood lipid level-related diseases, e.g., hyperlipidemia, arteriosclerosis, angina pectoris, stroke and hepatic diseases; the ACAT activity; and the HMG-CoA reductase activity. Further, in spite of their potent efficacies, the inventive flavanone derivatives exhibit no toxicity or mitogenicity in tests using mice.

A pharmaceutical formulation may be prepared by using the compositions of the invention in accordance with any of the conventional procedures. In preparing the formulation, the active ingredient is preferably admixed or diluted with a carrier, or enclosed within a carrier which may be in the form of a capsule, sachet or other container. When the carrier serves as a diluent, it may be a solid, semi-solid or liquid material acting as a vehicle, excipient or medium for the active ingredient. Thus, the formulations may be in the form of a tablet, pill, powder, sachet, elixir, suspension, emulsion, solution, syrup, aerosol, soft and hard gelatin capsule, sterile injectable solution, sterile packaged powder and the like.

Examples of suitable carriers, excipients, and diluents are lactose, dextrose, sucrose, sorbitol, mannitol, starches, gum acacia, alginates, gelatin, calcium phosphate, calcium silicate, cellulose, methyl cellulose, microcrystalline cellulose, polyvinylpyrrolidone, water, methylhydroxybenzoates, propylhydroxybenzoates, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a mammal by employing any of the procedures well known in the art.

The pharmaceutical composition of the present invention can be administered via various routes including oral, transdermal, subcutaneous, intravenous and intramuscular introduction. In case of human, a typical daily dose of the flavanone derivative of formula (I) may range from about 0.1 to 50 mg/kg body weight, preferably 1 to 10 mg/kg body weight, and can be administered in a single dose or in divided doses.

However, it should be understood that the amount of the active ingredient actually administered ought to be determined in light of various relevant factors including the condition to be treated, the chosen route of administration, the age, sex and body weight of the individual patient, and the severity of the patient's symptom; and, therefore, the above dose should not be intended to limit the scope of the invention in any way.

Moreover, the flavanone derivative of formula (I) can be incorporated in foods or beverages, as an additive or a dietary supplement, for the purpose of treating or preventing elevated blood lipid level-related diseases, and inhibiting the ACAT and the HMG-CoA reductase activities. The foods or beverages may include meats; juices such as a vegetable juice(e.g., carrot juice and tomato juice) and a fruit juice (e.g., orange juice, grape juice, pineapple juice, apple juice and banana juice); chocolates; snacks; confectionery; pizza; foods made from cereal flour such as breads, cakes, crackers, cookies, biscuits, noodles and the likes; gums; dairy products such as milk, cheese, yogurt and ice creams; soups; broths; pastes, ketchups and sauces; teas; alcoholic beverages; carbonated beverages such as Coca-Cola® and Pepsi-Cola®; vitamin complexes; and various health foods.

In this case, the content of the flavanone derivative of formula (I) in a food or beverage may range from 0.01 to 20% by weight, preferably 0.1 to 10% by weight.

The following Examples are intended to further illustrate the present invention without limiting its scope.

As described above, flavanone derivatives can be used as an effective, non-toxic pharmaceutical agent for treating or preventing elevated blood lipid level-related diseases, inhibiting the ACAT activity and/or inhibiting the HMG-CoA reductase activity.

Further, percentages given below for solid in solid mixture, liquid in liquid, and solid in liquid are on a wt/wt, vol/vol and wt/vol basis, respectively, and all the reactions were carried out at room temperature, unless specifically indicated otherwise.

Example 1

Preparation and Analysis of Naringenin 7-O-cetyl Ether(Compound 4, NG5006)

10 g(36.73 mmol) of naringenin was dissolved in a mixture of 100 ml of acetone and 100 ml of dimethylformamide(DMF). 13.5 ml of hexadecanyl bromide and 4.70 g of sodium carbonate were added to the mixture and stirred in a water bath at 80° C. for 12 hours. The resulting solution was cooled, and then, 100 ml of water and 800 ml of EtOAc were added thereto and the mixture was extracted with EtOAc. The extract thus obtained was washed with water and concentrated under a reduced pressure. The solid formed was filtered using a glass filter and dried under a reduced pressure to give 10.1 g of naringenin 7-O-cetyl ether. Further, the residue was concentrated and subjected to silica gel column chromatography(45 mm×150 mm, 70–230 mesh, eluent: hexane/EtOAc(8:2)) to obtain an additional 3g of naringenin 7-O-cetyl ether as a pale yellow solid (Yield: 72%).

melting point(m.p.): 114–117° C.

$^1$H NMR (CDCl$_3$) δ 12.0 (s, 1H), 7.32 (d, J=8.4 Hz, 2H), 6.87 (d, J=8.4 Hz, 2H), 6.04 (d, J=2.0 Hz, 1H), 6.02 (d, J=2.0 Hz, 1H), 5.33 (dd, J=13.2, 2.8 Hz, 1H), 3.95 (t, J=6.8 Hz, 2H), 3.07 (dd, J=17.2, 13.2 Hz, 1H), 2.77 (dd, J=17.2, 2.8 Hz, 1H), 1.75 (quin, J=6.8 Hz, 2H), 1.44–1.36 (m, 2H), 1.34–1.22 (m, 24H), 0.87 (t, J=6.8 Hz, 3H) ppm.

$^{13}$C NMR (CDCl$_3$) δ 195.8, 167.6, 164.0, 162.8, 156.0, 130.6, 127.9, 115.6, 103.0, 95.6, 94.6, 78.9, 68.6, 43.2, 32.0, 29.75–29.69 (six carbons), 29.62, 29.57, 29.4, 29.3, 28.9, 25.9, 22.7, 14.2 ppm.

1D NOESY: NOE contacts were observed between H (6.04 and 6.02 ppms) and H (3.95 ppm).

EXAMPLE 2

Preparation and Analysis of Naringenin 7-O-stearyl Ether(Compound 7)

10 g(36.73 mmol) of naringenin was dissolved in a mixture of 20 ml of acetone and 20 ml of DMF. 1.5 ml of octadecanyl bromide and 470 mg of sodium carbonate were added to the mixture and stirred in a water bath at 80° C. for 19 hours. The resulting solution was cooled, and then, 20 ml of water and 200 ml of EtOAc were added thereto and the mixture was extracted with EtOAc. The extract thus obtained was washed with water and concentrated under a reduced pressure. A small amount of MeOH was added to the solid thus formed and the mixture was stirred with glass stick. The solid thus obtained was filtered and washed with EtOAc to give 1.25 g of naringenin 7-O-stearyl ether as a very pale yellow solid.

m.p.: 117–119° C $^1$H NMR (CDCl$_3$) δ 12.0 (s, 1H), 7.32 (d, J=8.4 Hz, 2H), 6.87 (d, J=8.4 Hz, 2H), 6.04 (d, J=2.0 Hz, 1H), 6.02 (d, J=2.0 Hz, 1H), 5.34 (dd, J=12.8, 2.8 Hz, 1H), 3.94 (t, J=6.8 Hz, 2H), 3.07 (dd, J=17.2, 12.8 Hz, 1H), 2.77 (dd, J=17.2, 2.8 Hz, 1H), 1.75 (quin, J=6.8 Hz, 2H), 1.44–1.36 (m, 2H), 1.34–1.22 (m, 28H), 0.89 (t, J=6.8 Hz, 3H) ppm.

$^{13}$CNMR(CDCl$_3$) δ 195.8, 167.5, 164.0, 162.7, 156.0, 130.6, 127.9, 115.6, 103.0, 95.5, 94.6, 78.9, 68.6, 43.2, 32.0, 29.74–29.65 (8 carbons), 29.62, 29.57, 29.4, 29.3, 28.9, 25.9, 22.7, 14.2 ppm.

1D NOESY: NOE contacts were observed between H (6.04 and 6.02 ppms) and H (3.94 ppm).

EXAMPLE 3

Preparation and Analysis of Hesperetin 7-cetyl Ether(Compound 9)

100 mg of hesperetin and 40 mg of sodium carbonate were dissolved in a dryed DMSO, and then, 0.15 ml of hexadecanyl bromide was added thereto. The mixture was stirred at 80° C. for 18 hours. The resulting solution was cooled and diluted with EtOAc, and then, washed with water and saline. The resulting solution thus obtained was dried with anhydrous magnesium sulfate and concentrated. The solid thus formed was triturated with EtOAc/hexane to give 180 mg of hesperetin 7-cetyl ether as a very pale yellow solid.

m.p.: 106–108° C.

$^1$H NMR (CDCl$_3$) δ 12.0 (s, 1H), 7.04 (d, J=2.0 Hz, 1H), 6.93 (dd, J=8.4, 2.4 Hz, 1H), 6.88 (d, J=8.4 Hz, 1H), 6.05 (d, J=2.0 Hz, 1H), 6.02 (d, J=2.0 Hz, 1H), 5.32 (dd, J=13.2, 3.2 Hz, 1H), 3.95 (t, J=6.4 Hz, 2H), 3.07 (dd, J=17.2, 13.2 Hz, 1H), 2.78 (dd, J=17.2, 3.2 Hz, 1H), 1.75 (quin, J=7.2 Hz, 2H), 1.40 (m, 2H), 1.32–1.20 (m, 24H), 0.87 (t, J=6.4 Hz, 3H) ppm.

1D NOESY: NOE contacts were observed between H (6.05 and 6.02 ppms) and H (3.95 ppm).

EXAMPLE 4

Preparations and Analyses of Naringenin 7-O-oleic Acid Monoester(compound 12) and 7,4'-O-oleic Acid Diester(Compound 13)

500 mg of naringenin and 0.2 ml of triethylamine were dissolved in 7 ml of dried tetrahydrofuran(THF) and the mixture was cooled with an ice water. 0.6 ml of oleoyl chloride was added dropwise to the resulting solution. The mixture thus obtained was stirred at room temperature for 3 hours. The resulting solution was diluted with EtOAc and washed with a saturated sodium hydrogen carbonate solution, followed by washing with saline. The resulting solution was dried with anhydrous magnesium sulfate, filtered, and concentrated. The residue was subjected to silica gel column chromatography(25 mm×150 mm, 70–230 mesh, eluent: hexane/EtOAc (9: 1)) to give 527 mg of 7-O-oleic monoester and 57 mg of 7,4'-O-oleic acid diester as colorless liquids.

7-O-oleic acid monoester

Viscous liquid $^1$H NMR (CDCl$_3$) δ 11.9 (s, 1H), 7.28 (d, J=8.8 Hz, 2H), 6.85 (d, J=8.8 Hz, 2H), 6.28 (d, J=2.0 Hz, 1H), 6.26 (d, J =2.0 Hz, 1H), 5.38–5.31 (m, 3H), 3.11 (dd, J=17.2, 13.2 Hz, 1H), 2.80 (dd, J=17.2, 2.8 Hz, 1H), 2.53 (t, J=7.6 Hz, 2H), 2.00 (m, 4H), 1.71 (quin, J=7.2 Hz, 2H), 1.40–1.20 (m, 22H), 0.87 (t, J=6.0 Hz, 3H) ppm.

$^{13}$C NMR(CDCl$_3$) δ 197.2, 171.4, 163.1, 162.3, 158.3, 156.3, 130.0, 129.7, 129.6, 127.8, 115.6, 106.1, 103.1, 101.7, 79.0, 43.3, 34.4, 31.9, 29.8, 29.7, 29.5, 29.3, 29.2, 29.13, 29.07, 29.0, 27.23, 27.16, 24.8, 22.7, 14.2 ppm.

1D NOESY: NOE contacts were observed between H (6.28 and 6.26 ppms) and H (2.53 ppm).

7,4'-O-oleic acid diester

Viscous liquid $^1$H NMR (CDCl$_3$) δ 11.8 (s, 1H), 7.45 (d, J=8.8 Hz, 2H), 7.14 (d, J=8.8 Hz, 2H), 6.30 (d, J=2.0 Hz, 1H), 6.28 (d, J=2.0 Hz, 1H), 5.45 (dd, J=13.6, 2.8 Hz, 1H), 5.40–5.32 (m, 4H), 3.10 (dd, J=17.2, 13.6 Hz, 1H), 2.86 (dd, J=17.2, 2.8 Hz, 1H), 2.54 (m, 4H), 2.02 (m, 8H), 1.76 (m, 4H), 1.40–1.20 (m, 44H), 0.87 (t, J=6.0 Hz, 6H) ppm.

$^{13}$C NMR (CDCl$_3$) δ 196.6, 172.1, 171.0, 163.2, 162.0, 158.4, 151.0 135.3, 130.0, 129.6, 127.2, 122.1, 106.1, 103.4, 101.7, 78.7, 43.6, 34.4, 31.9, 29.7–29.1(16 carbons), 27.3, 27.2, 24.9, 24.8, 22.7, 14.3, 14.2 ppm.

Example 5

Preparation and Analysis of Naringenin 5,7,4'-O-oleic Acid Triester(Compound 14)

100 mg of naringenin and 1 ml of oleoyl chloride were dissolved in 7 ml of dried THF and the mixture was cooled with an ice water. 0.5 ml of triethylamine was added dropwise to the resulting solution and the mixture was stirred at room temperature for 5 hours. The resulting solution was diluted with EtOAc and washed with a saturated sodium hydrogen carbonate solution, followed by washing with saline. The resulting solution was dried with anhydrous magnesium sulfate, filtered, and concentrated. The concentrate was subjected to silica gel column chromatography(25 mm×150 mm, 70–230 mesh, eluent: hexane/EtOAc(9:1)) to give 203 mg of naringenin 5,7,4'-O-oleic acid triester as coloress viscous liquid.

$^1$H NMR (CDCl$_3$) & 7.44 (d, J=8.8 Hz, 2H), 7.13 (d, J=8.8 Hz, 2H), 6.76 (d, J=2.0 Hz, 1H), 6.50 (d, J=2.0 Hz, 1H), 5.47 (dd, J=13.6, 2.8 Hz, 1H), 5.40–5.30 (m, 6H), 3.00 (dd, J=17.2, 13.6 Hz, 1H), 2.75 (dd, J=17.2, 2.8 Hz, 1H), 2.66 (m, 2H), 2.55 (m, 4H), 2.00 (m, 12H), 1.74 (m, 6H), 1.40–1.20 (m, 66H), 0.87 (m, 9H) ppm.

EXAMPLE 6

Preparation and Analysis of Naringenin 5,7,4'-O-benzoic Acid Triester(Compound 20)

The procedure of Example 5 was repeated by using 100 mg of naringenin and 0.21 ml of benzoyl chloride to obtain 209 mg of naringenin 5,7,4'-O-benzoic acid triester as a white solid. Finally, the solid was triturated with hexane.

m.p.: 126–129° C.

¹H NMR (CDCl₃) & 8.24–8.16 (m, 6H), 7.68–7.60 (m, 3H), 7.54–7.49 (m, 8H), 7.29 (d, J=8.8 Hz, 2H), 6.99 (d, J=2.0 Hz, 1H), 6.83 (d, J=2.0 Hz, 1H), 5.58 (dd, J=13.6, 2.8 Hz, 1H), 3.09 (dd, J=16.8, 13.6 Hz, 1H), 2.81 (dd, J=16.8, 2.8 Hz, 1H) ppm.

¹³C NMR (CDCl₃) & 188.7, 164.9, 164.8, 163.8, 163.2, 156.2, 151.5,151.1, 135.7, 134.1, 133.7, 133.5, 132.0, 130.3, 129.4, 129.2, 128.7, 128.55,128.52, 127.4, 127.3, 122.2, 112.0, 111.1, 109.4, 79.1,45.2 ppm.

EXAMPLE 7

Preparation and Analysis of Naringenin 5,7,4'-O-(p-chlorobenzoic Acid) Triester(Compound 21)

The procedure of Example 5 was repeated by using 100 mg of naringenin and 0.21 ml of p-chlorobenzoyl chloride to obtain 316 mg of naringenin 5,7,4'-O-(p-chlorobenzoic acid) triester as a white solid. Finally, the solid was triturated with EtOAc/hexane.

m.p.: 189–191° C.

¹H NMR (CDCl₃) δ 8.15 (d, J=8.8 Hz, 2H), 8.13 (d, J=8.8 Hz, 2H), 8.10 (d, J=8.8 Hz, 2H), 7.53–7.48 (m, 8H), 7.28 (d, J=8.8 Hz, 2H), 6.98 (d, J=2.0 Hz, 1H), 6.81 (d, J=2.0 Hz, 1H), 5.58 (dd, J=13.6, 2.4 Hz, 1H), 3.07 (dd, J=16.4, 13.6 Hz, 1H), 2.80 (dd, J=16.4, 2.8 Hz, 1H) ppm.

¹³CNMR(CDCl₃) δ 188.7, 164.1, 164.0, 163.2, 163.0, 155.9, 151.2, 150.9, 140.8, 140.3, 140.1, 135.7, 131.8, 131.7, 131.6, 131.5, 129.3, 129.1, 128.94, 128.92, 127.8, 127.6, 127.4, 126.9, 122.1, 111.9, 110.9, 109.5, 79.1, 45.2 ppm.

Example 8

Preparation and Analysis of Naringenin 5,7,4'-O-(o-chlorobenzoic Acid) Triester(Compound 22)

The procedure of Example 5 was repeated by using 100 mg of naringenin and 0.233 ml of o-chlorobenzoyl chloride to obtain 100 mg of naringenin 5,7,4'-O-(o-chlorobenzoic acid) triester as a white solid. Finally, the solid was triturated with EtOAc/hexane.

m.p.: 121–124° C.

¹H NMR (CDCl₃) & 8.29 (dd, J=8.0, 1.2 Hz, 1H), 8.05 (dd, J=8.0, 0.8 Hz, 1H), 8.03 (dd, J=8.0, 0.8 Hz, 1H), 7.56–7.48 (m, 8H), 7.45–7.38 (m, 3H), 7.33 (d, J=8.8 Hz, 2H), 7.03 (d, J=2.4 Hz, 1H), 6.86 (d, J=2.4 Hz, 1H), 5.59 (dd, J=13.6, 2.4 Hz, 1H), 3.10 (dd, J=16.8, 13.6 Hz, 1H), 2.84 (dd, J=16.8, 2.4 Hz, 1H) ppm.

¹³C NMR (CDCl₃) & 188.8, 163.8, 163.13, 163.09, 162.5, 155.8, 151.0, 150.9, 135.8, 134.7, 134.6, 134.4, 133.7, 133.3, 133.2, 132.6, 132.0, 131.9, 131.5, 131.3, 131.1, 128.9, 128.7, 128.1, 127.4, 126.8, 126.7, 122.1, 112.1, 110.9, 109.6, 79.1, 45.2 ppm.

EXAMPLE 9

Preparation and Analysis of Naringenin 5,7,4'-O-(o-methoxybenzoic Acid) Triester(Compound 23)

The procedure of Example 5 was repeated by using 100 mg of naringenin and 0.233 ml of o-methoxybenzoyl chloride to obtain 100 mg of naringenin 5,7,4'-O-(o-methoxybenzoic acid) triester as a white solid. Finally, the solid was subjected to silica gel chromatography(25 mm×150 mm, 70–230 mesh, eluent: EtOAc/hexane(3:7)).

m.p.: 84–87° C.

¹H NMR (CDCl₃) δ 8.23 (dd, J=7.6, 1.6 Hz, 1H), 8.02 (dd, J=7.6, 2.0 Hz, 1H), 7.97 (dd, J=8.4,2.0 Hz, 1H), 7.58–7.52 (m, 3H), 7.50 (d, J=8.4 Hz, 2H), 7.29 (d, J=8.4 Hz, 2H), 7.09–7.02 (m, 6H), 7.33 (d, J=8.8 Hz, 2H), 6.97 (d, J=2.0 Hz, 1H), 6.81 (d, J=2.0Hz, 1H), 5.55 dd, J=13.6, 2.4 Hz, 1H), 3.93 (s, 9H), 3.07 (dd, J=16.4, 13.6 Hz, 1H), 2.80 (dd, J=176.4, 2.4 Hz, 1H) ppm.

¹³C NMR (CDCl₃) δ 188.9, 164.1, 163.4, 163.0, 162.8, 160.0, 159.9, 159.8, 156.2, 151.4, 151.1, 135.6, 134.8, 134.4, 134.3, 132.8, 132.3, 132.2, 127.2, 122.3, 120.21, 120.18, 120.14, 118.7, 118.6, 118.0, 112.1, 112.0, 111.9, 111.4, 109.3, 79.1, 56.04, 56.02, 45.3 ppm.

EXAMPLE 10

Preparation and Analysis of Naringenin 5,7,4'-O-P-methoxybenzoic Acid) Triester(compound 24)

The procedure of Example 5 was repeated by using 100 mg of naringenin and 0.273 ml of p-methoxybenzoyl chloride to obtain 100 mg of naringenin 5,7,4'-O-(p-methoxybenzoic acid) triester as a white solid. Finally, the solid was triturated with hexane.

m.p.: 113–117° C.

¹H NMR (CDCl₃) & 8.17 (d, J=8.8 Hz, 2H), 8.15 (d, J=8.8 Hz, 2H), 8.12 (d, J=8.8 Hz, 2H), 7.51 (d, J=8.8 Hz, 2H), 7.27 (d, J=8.8 Hz, 2H), 7.01–6.95 (m, 7H), 6.80 (d, J=2.0 Hz, 1H), 5.56 (dd, J=13.6, 2.8 Hz, 1H), 3.892 (s, 3H), 3.890 (s, 3H), 3.888 (s, 3H), 3.07 (dd, J=16.4, 13.6 Hz, 1H), 2.78 (dd, J=16.4, 2.8 Hz, 1H) ppm.

¹³C NMR (CDCl₃) & 188.8, 164.6, 164.5, 164.2, 163.9, 163.8, 163.5, 163.1, 156.3, 151.6, 151.2, 135.6, 132.4, 132.3, 127.3, 122.2, 121.8, 121.5, 120.8, 113.9, 111.9, 111.2, 109.2, 55.6, 55.55, 55.53, 45.3 ppm.

EXAMPLE 11

Preparation and Analysis of Naringenin 5,7,4'-O-(1-naphtoxic Acid) Triester(Compound 27)

The procedure of Example 5 was repeated by using 100 mg of naringenin and 0.35 ml of 1-naphtoxic acid to obtain 100 mg of naringenin 5,7,4'-O-(1-naphtoxic acid) triester as a white solid. Finally, the solid was triturated with EtOAc/hexane.

m.p.: 165–167° C.

¹H NMR (CDCl₃) δ 8.44 (br s, 1H), 8.79 (br s, 1H), 8.78 (br d, J=0.8 Hz, 1H), 8.23 (dd, J=8.8, 2.0 Hz, 1H), 8.19 (dd, J 8.8, 2.0 Hz, 1H), 8.16 (dd, J=8.8, 2.0 Hz, 1H), 8.02–7.91 (m, 9H), 7.67–7.55 (m, 8H), 7.35 (d, J=8.4 Hz, 2H), 7.09 (d, J=2.4 Hz, 1H ), 6.95 (d, J=2.4 Hz, 1H), 5.63 (dd, J=13.6, 2.8 Hz, 1H), 3.12 (dd, J=16.8, 13.6 Hz, 1H), 2.85 (dd, J=16.8, 2.8 Hz, 1H) ppm.

¹³CNMR (CDCl₃) δ 188.8, 165.1, 165.0, 164.0, 163.2, 156.3, 151.6, 151.2, 135.9, 135.82, 135.78, 135.7, 132.5, 132.38, 132.34, 132.3, 132.2, 132.0, 129.54, 129.50, 129.4, 129.4, 128.9, 128.7, 128.6, 128.5, 128.38, 128.36, 127.80, 127.78, 127.74, 127.4, 127.0, 126.8, 126.62, 126.60, 126.4, 125.7, 125.5, 125.3, 125.2, 122.2, 112.2, 111.1, 109.5, 79.2,45.3 ppm.

EXAMPLE 12

Decrease of Plasma Cholesterol, HDL-Cholesterol and Triglyceride Lipid Levels in Compound 4 (NG5006)-Fed Rats (Step 1) Administration of NG5006 to rats 30 four-week-old white Sprague-Dawley rats (Korea Institute of Science and Technology, Korea), each weighing about 90 to 120 g, were evenly divided into three dietary groups by a randomized block design. The rats of the three groups were fed with three different high-cholesterol diets, i.e., AIN-76 laboratory animal diet(ICN Biochemicals, Cleveland, Ohio, U.S.A.) containing 1% cholesterol(Control group), 1% cholesterol plus 0.02% naringenin and 1% cholesterol plus 0.036% NG5006, respectively. The compositions of the diets fed to the three groups are shown in Table II.

TABLE II

| Dietary group Component | Control group (n = 10) | Naringenin group (n = 10) | NG5006 group (n = 10) |
|---|---|---|---|
| Casein | 20 | 20 | 20 |
| D,L-methionine | 0.3 | 0.3 | 0.3 |
| Corn starch | 15 | 15 | 15 |
| Sucrose | 49 | 48.98 | 48.964 |
| Cellulose powder | 5 | 5 | 5 |
| Mineral mixture[*1] | 3.5 | 3.5 | 3.5 |
| Vitamin mixture[*1] | 1 | 1 | 1 |
| Choline bitartrate | 0.2 | 0.2 | 0.2 |
| Corn oil | 5 | 5 | 5 |
| Cholesterol | 1 | 1 | 1 |
| Naringenin[*2] | — | 0.02 | — |
| NG5006 | — | — | 0.036 |
| Total | 100 | 100 | 100 |

[*1]Purchased from TEKLAD premier Co. (Madison, WI, U.S.A.)
[*2]Purchased from Sigma Chemical Co. (St. Louis, MO, U.S.A.)

The rats were allowed to feed freely on the specified diet together with water for six weeks, the ingestion amount was recorded daily and the rats were weighed every 7 days, and then the record was analyzed. All rats showed a normal growth rate and there were observed no significant difference among the three groups in terms of the feed ingestion amount and the weight gain. (Step 2) Determination of total cholesterol, HDL-cholesterol and triglyceride contents in blood The effects of administering naringenin or NG5006 to rats on the plasma cholesterol and triglyceride contents were determined as follows.

Blood samples were taken from the rats of the three dietary groups and total cholesterol level was determined by using Sigma Diagnostic Kit Cat. No. C0534(Sigma Chemical Co., U.S.A.). HDL fractions were separated therefrom by using HDL-cholesterol reagent(Sigma Chemical Co., Cat. No. 352-1) and HDL-cholesterol level was determined by using Sigma Diagnostic Kit Cat. No. C9908(Sigma Chemical Co., U.S.A.). Triglyceride level was determined by using Sigma Diagnostic Kit Cat. No. 336-10(Sigma Chemical Co., U.S.A.). The result is shown in Table III.

TABLE III

| Group Lipid Conc. | Control group | Naringenin group | NG5006 group |
|---|---|---|---|
| Total-C (mg/dl) | 226.8 ± 14.0 | 190.6 ± 7.6 | 183.5 ± 6.4 |
| HDL-C (mg/dl) | 30.6 ± 2.0 | 35.8 ± 1.5 | 36.7 ± 1.3 |
| HDL-C ------(%) Total-C | 13.5 ± 1.2 | 18.8 ± 0.9 | 20.4 ± 0.7 |
| TG(mg/dl) | 153.0 ± 8.9 | 143.7 ± 9.4 | 118.4 ± 3.4 |
| AI | 6.4 ± 0.5 | 4.3 ± 0.3 | 4.0 ± 0.2 |

* Total-C: Total-cholesterol
* HDL-C: HDL-cholesterol
* TG: Triglyceride
* AI: Atherosclerosis Index (AI = (Total-C − HDL-C)/HDL-C)

As can be seen in Table III, the total plasma cholesterol level is lower by 19% and 16% in NG5006 and the naringenin groups, respectively, than in the Control group. Further, the triglyceride level is lower by 33% and 6% in the NG5006 and the naringenin groups, respectively, than in the control group. This result demonstrates that NG5006 is superior to naringenin in lowering blood lipid level.

EXAMPLE 13

Inhibitions of ACAT and HMG-CoA Reductase Activities in NG5006-Fed Rats (Step 1) Preparation of microsomes To determine the effect of feeding NG5006 to rats on the activities of ACAT and HMG-CoA reductase, microsomes were separated from liver tissues to be used as an enzyme source.

1 g each of the livers taken from each group of rats of Example 12 was homogenized in 5 ml of homogenization medium(0.1 M $KH_2PO_4$, pH 7.4, 0.1 mM EDTA and 10 mM β-mercaptoethanol). The homogenate was centrifuged at 3,000×g for 10 min. at 4° C. and the supernatant thus obtained was centrifuged at 15,000×g for 15 min. at 4° C. to obtain a supernatant. The supernatant was put into an ultracentrifuge tube(Beckman) and centrifuged at 100,000×g for 1 hour at 4° C. to obtain microsomal pellets, which were then suspended in 3 ml of the homogenization medium and centrifuged at 100,000×g for 1 hour at 4° C. The pellets thus obtained were suspended in 1 ml of the homogenization medium. The protein concentration of the resulting suspension was determined by Lowry's method and then adjusted to 4 to 8 mg/ml. The resulting suspension was stored in a deep freezer(Biofreezer, Forma Scientific Inc.).

(Step 2) ACAT assay 6.67 μl of 1 mg/ml cholesterol solution in acetone was mixed with 6 μl of 10% Triton WR-1339(Sigma Co.) in acetone and then, acetone was removed from the mixture by evaporation under a nitrogen flow. Distilled water was added to the resulting mixture to adjust the concentration of cholesterol to 30 mg/ml.

Added to 10 μl of the resulting aqueous cholesterol solution were 10 μl of 1 M $KH_2PO_4$(pH 7.4), 5 μl of 0.6 mM bovine serum albumin(BSA), 10 μl of microsome solution obtained in (Step 1) and 55 μl of distilled water(total 90 μl). The mixture was pre-incubated in a water bath at 37° C. for 30 min.

10 μl of [1-$^{14}$C] oleyl-CoA solution(0.05 μCi, final concentration: 10 μM) was added to the pre-incubated mixture and the resulting mixture was incubated in a water bath at 37° C. for 30 min. Added to the mixture were 500 μl of isopropanol:heptane mixture(4:1(v/v)), 300 μl of heptane and 200 μl of 0.1 M $KH_2PO_4$(pH 7.4), and the mixture was mixed vigorously using a vortex mixer and then allowed to stand at room temperature for 2 min.

200 μl of the resulting supernatant was put in a scintillation bottle and 4 ml of scintillation fluid(Lumac Co.) was added thereto. The mixture was assayed for radioactivity with 1450 Microbeta liquid scintillation counter(Wallac Co., Finland). ACAT activity was calculated as picomoles of cholesteryl oleate synthesized per min. per mg protein (pmoles/min/mg protein). The result is shown in Table IV.

(Step 3) HMG-CoA reductase assay

The activity of HMG-CoA reductase was determined by employing [$^{14}$C]HMG-CoA, in accordance with the method of Shapiro et al.(*Biochemica et Biophysica Acta*, 370, 369–377(1974)) as follows.

The enzyme in the supernatant containing the microsome obtained in (Step 1) was activated at 37° C. for 30 min. Added to a reaction tube were 20 μl of HMG-CoA reductase assay buffer(0.25M KH$_2$PO$_4$(pH 7.0), 8.75 mM EDTA, 25 mM DTT, 0.45 M KCl and 0.25 mg/ml BSA), 5 μl of 50 mM NADPH, 5 μl of [$^{14}$C]HMG-CoA(0.05μ Ci/tube, final conc. 120μM), and 10 μl of activated microsomal enzyme (0.03–0.04 mg), and the mixture was incubated at 37° C. for 30 min. The reaction was terminated by adding 10 μl of 6 M HCl to the mixture, and the mixture was incubated at 37° C. for 15 min. to allow complete lactonization of the product (mevalonate). The precipitate was removed by centrifugation at 10,000×g for 1 min. and the supernatant was applied to a Silica gel 60G TLC plate(Altech, Inc., Newark, U.S.A.) and then developed with benzene:acetone(1:1, v/v). A region having a R$_f$ value ranging from 0.65 to 0.75 was removed by scraping with a disposable cover slips and assayed for radioactivity with 1450 Microbeta liquid scintillation counter(Wallac Co., Finland). Enzyme activities were calculated as picomoles mevalonic acid synthesized per min. per mg protein(pmoles/min/mg protein). The result is shown in Table IV.

TABLE IV

| Group | Control Group | Naringenin group | NG5006 group |
|---|---|---|---|
| ACAT activity (pmole/min/mg protein) | 173.7 ± 6.3 | 153.3 ± 6.9 | 149.7 ± 5.1 |
| HMG-CoA reductase activity (pmole/min/mg protein) | 112.4 ± 8.7 | 87.7 ± 5.9 | 81.6 ± 6.0 |

As can be seen from Table IV, the control group rats showed relatively high ACAT and HMG-CoA reductase activities, while the ACAT and HMG-CoA activities observed in the NG5006-fed rat group are lower than that of the control group by 14% and 27.5%, respectively.

EXAMPLE 14

Inhibition of Arteriosclerosis in NG5006-Fed Rabbits (Step 1) Administration of NG5006 to rabbits 22 three-month-old New Zealand White rabbits(Yeonam Horticulture and Animal Husbandry College, Korea) each weighing about 2.0 to 2.3 kg were bred under a condition of temperature 20±2° C., relative humidity 55±10%, and photoperiod 12L/12D. The rabbits were divided two groups of 6 rabbits and a group of 10 rabbits, and the rats of three groups were fed with three different diets, i.e., RC4 diet (Oriental Yeast Co., Japan) containing 1% cholesterol (Control group); 1% cholesterol plus 1 mg/kg Lovastatin® (Merck, U.S.A.)(Comparative group); and 1% cholesterol plus 0.1% NG5006, respectively. RC4 diet comprises 7.6% moisture, 22.8% crude protein, 2.8% crude fat, 8.8% crude ash, 14.4% crude cellulose and 43.6% soluble nitrogen-free substances. The rabbits were bred for 8 weeks while being allowed free access to the diets and water.

(Step 2) Analysis for fatty streak in the main artery

The rabbits bred in Step 1 were sacrificed and their chest were incised. The main artery was cut out therefrom in a length of about 5 cm downward from the site 1 cm above the aortic valve and the fat surrounding the main artery was removed. The main artery was incised in the middle along the longitudinal axis and fixed in 10% neutral buffered formalin for 24 hours, and then, pinned to a dish. The moist artery was photographed and, then, staining of fatty streak was carried out in accordance with the method of Esper, E., et al. (J. Lab. Clin. Med., 121, 103–110(1993)) as follows.

A part of the incised main artery was washed three times by 2 min. with anhydrous propylene glycol and stained for 30 min. with a saturated solution of Oil Red O(ORO, Sigma Co.) dissolved in propylene glycol. Thereafter, the artery was washed twice by 3 min. with 85% propylene glycol to remove remaining staining solution and, then washed with physical saline. The artery was photographed and the photograph was traced. The area of stained legion(fatty streak legion) was determined with an image analyzer(LEICA, Q-600, Germany) and its proportion(%) to the total arterial area was calculated. The result is shown in Table V. The results were tested by student t-test by using Microsoft excel(version 7.0) program.

TABLE V

| Group | Control Group (n = 6) | Lovastatin ® Group (n = 6) | NG5006 Group (n = 10) |
|---|---|---|---|
| Fatty Streak lesion (%) | 61.8 ± 14.6 | 18.0 ± 9.5 | 12.3 ± 6.2 |

As can be seen from Table V, NG5006 and Lovastatin® groups significantly inhibit the formation of fatty streak as compared to the control group, while NG5006 group shows more superior result than Lovastatin® group.

Figure 1B:
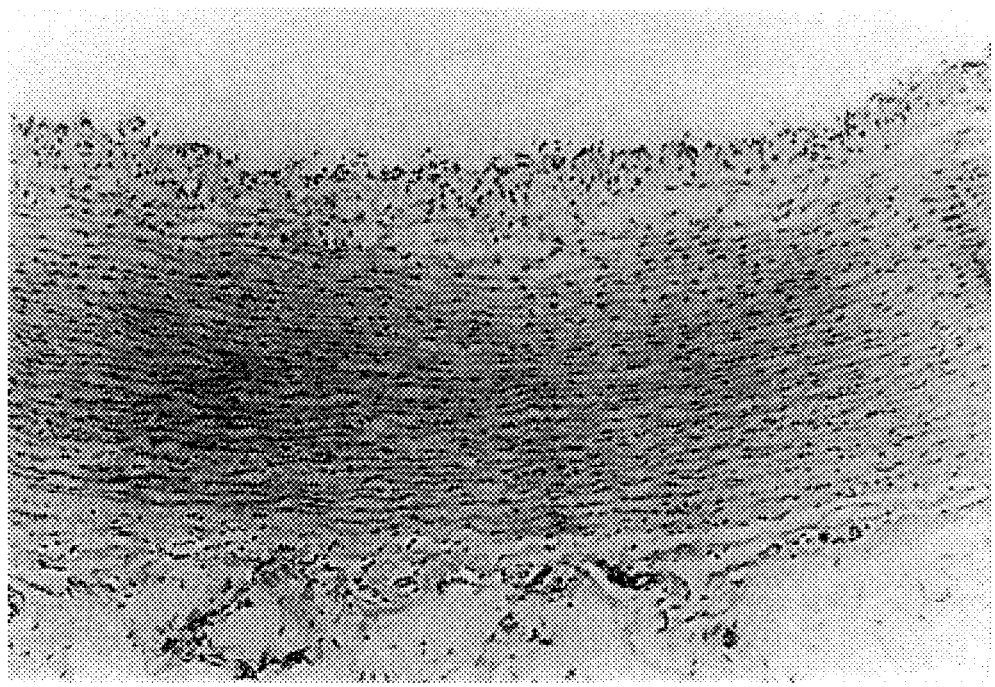
Figure 1C:
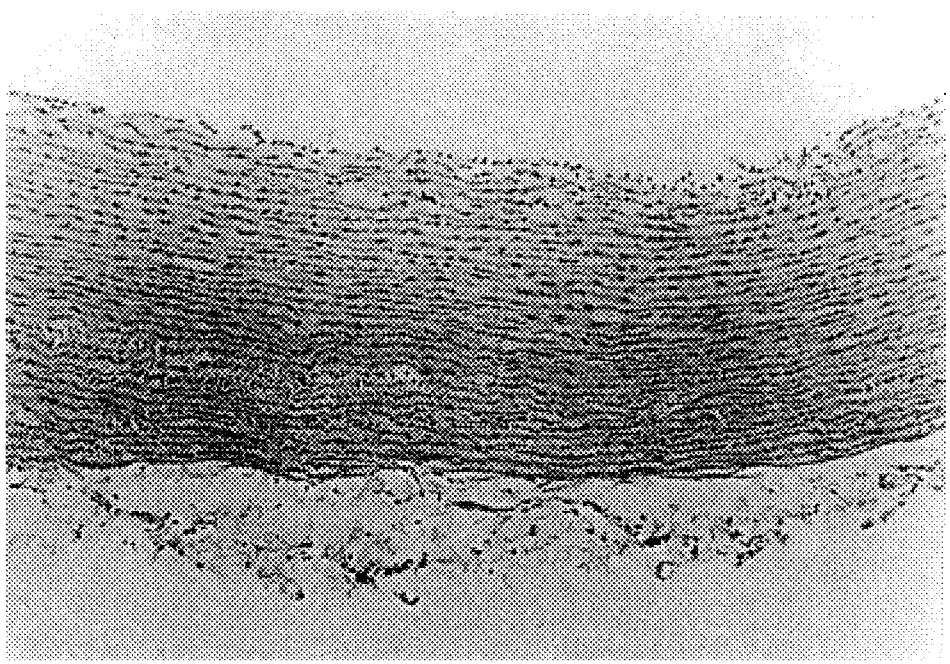

FIGS. 1A, 1B and 1C show the arteries of the rabbits administered with 1% cholesterol(control group); 1% cholesterol plus 1 mg/kg Lovastatin® (comparative group); and 1% cholesterol plus 0.1% NG5006, respectively. As shown in FIGS. 1A, 1B and 1C, a thick layer of fatty streak was observed on the arterial endothelium of the rabbit administered with 1% cholesterol, while no or very thin layers of macrophage-lipid complex were observed on the arterial endotheliums of the rabbits administered with 1% cholesterol plus 1 mg/kg Lovastatin® and 1% cholesterol plus 0.1% NG5006, respectively.

Accordingly, it is concluded that NG5006 strongly inhibits the arteriosclerosis even when the blood cholesterol level is very high.

(Step 3) Histologic observation of the organs

Portions of the main artery, heart, lung, liver, kidney and muscle were taken from each of the rabbits sacrificed in step 2 and visually examined to confirm that no pathogenic abnormality was found. One half of each portion of the organs was deep freezed and the other half was fixed in 10% neutral buffered formalin for more than 24 hours. The fixed organ piece was washed sufficiently with tap water, dehydrated stepwise with 70%, 80%, 90% and 100% ethanol and, then, embedded in a paraffin by employing SHANDON7 (Histocentre 2, U.S.A.). The embedded organ piece was sectioned in 4 μm thickness with a microtome(LSICA, RM2045, Germany) and stained with hematoxylin and eosin. The stained organ specimen was made transparent with xylene, mounted with permount, and then observed under a microscope to look for the presence of lesions. No lesion was observed in any of the organ specimen.

EXAMPLE 15

Prevention of Hepatic Diseases

In order to evaluate the effects of feeding a high cholesterol diet with NG5006 on liver tissues, the liver specimens taken from the sacrificed rabbit in Step 2 of Example 14 were treated in accordance with the procedure disclosed in Fogt F. and Nanji A., Toxicology and Applied Pharmacology, 136, 87–93, 1996; and Keegan A., et al., Journal of Hepatology, 23, 591–600, 1995, and observed under a microscope to be classified into four grades, i.e., 1+(0–25%), 2+(26–50%), 3+(51–75), 4+(76–100%) based on the proportion of abnormal fat-containing cells around the central vein in the liver acinus. The result is shown in Table VI. The results were tested by student t-test by using Microsoft excel(version 7.0) program.

TABLE VI

| Group | Control Group | Lovastatin ® Group | NG5006 Group |
|---|---|---|---|
| Proportion of abnormal fat-containing liver cells | 3.0 ± 0.7 | 3.3 ± 1.1 | 2.2 ± 0.9 |

As can be seen in Table VI, NG5006 significantly inhibits the formation of fatty liver as compared to the Control and the Lovastatin® group.

Figure 2A:
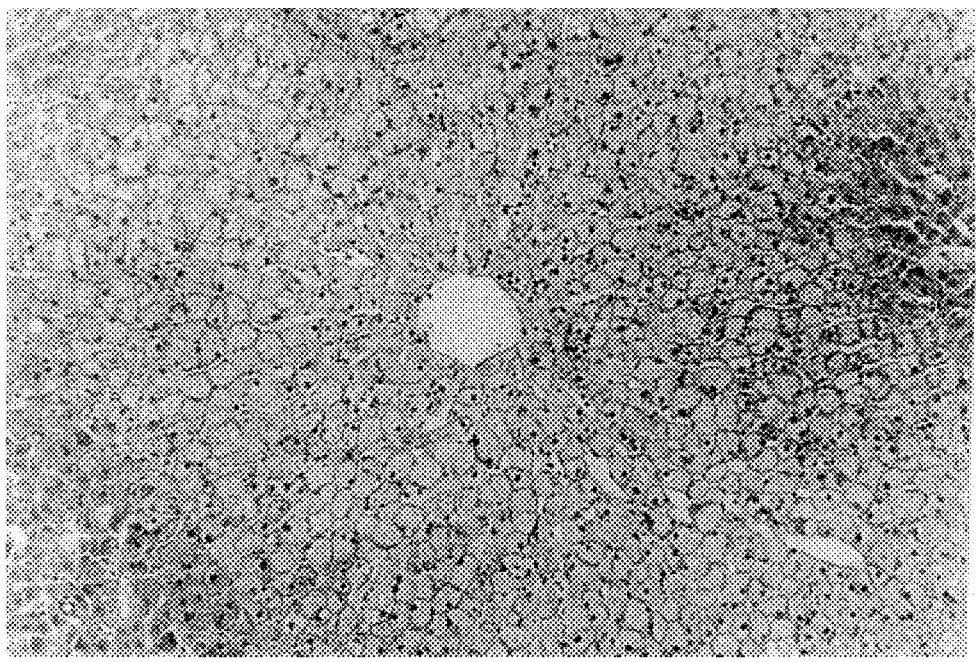
FIGS. 2A, 2B and 2C present the microscopic features of the livers of the rabbits administered with 1% cholesterol (control); 1% cholesterol plus 1 mg/kg Lovastatin®; and 1% cholesterol plus 0.1% NG5006, respectively.
Figure 2B:
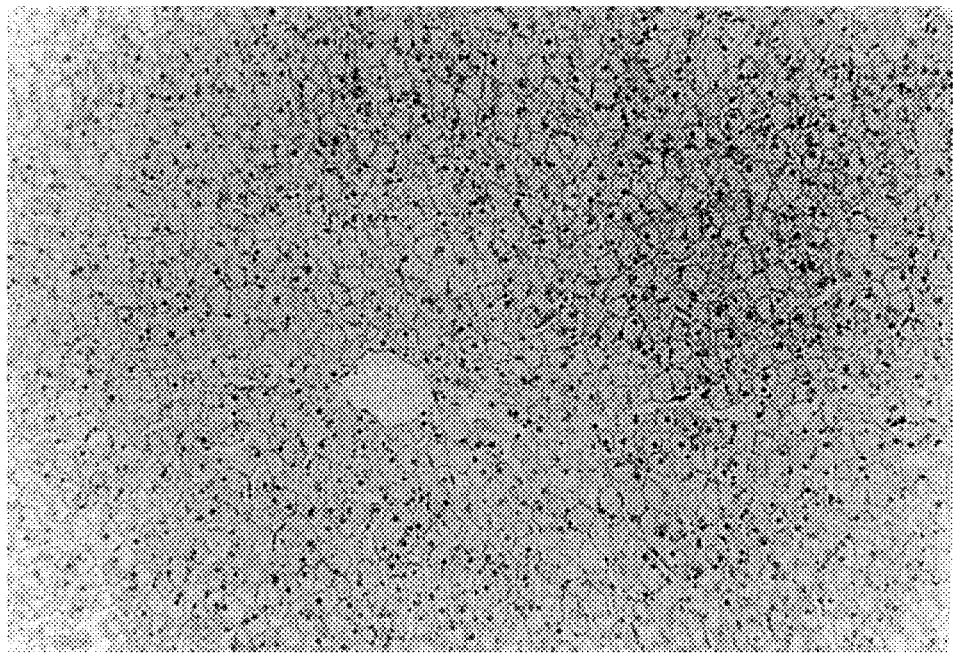
Figure 2C:
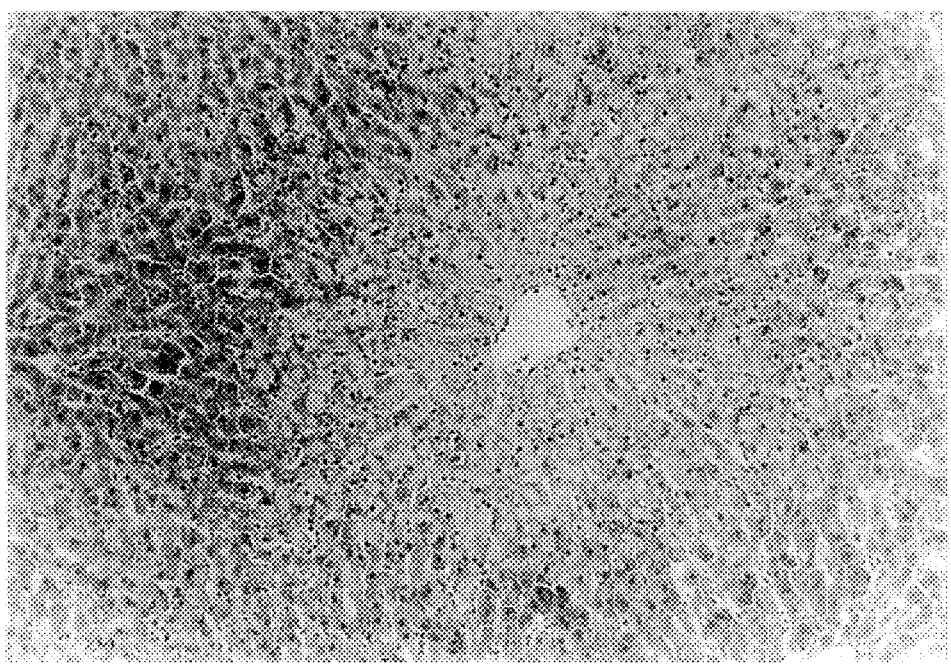

FIGS. 2A, 2B and 2C present the microscopic features of the livers of the rabbits administered with 1% cholesterol (control); 1% cholesterol plus 1 mg/kg Lovastatin®; and 1% cholesterol plus 0.1% NG5006, respectively. In FIGS. 2A and 2B, many cells containing excessive fat were observed around the central vein. In contrast, almost all liver cells are of a normal shape in FIGS. 2C, which suggested that NG5006 can significantly inhibit the formation of fatty liver.

As can be seen from the above, the administration of NG5006 can inhibit the development of fatty liver.

Example 16

Inhibition of ACAT Activity in NG5006-Fed Rabbits

The effect of feeding NG5006 to rabbits on the activities of ACAT was determined using the rabbits bred in Step 1 of Example 14 in accordance with procedure disclosed in step 1 of Example 13. The result is shown in Table VII.

TABLE VII

| Group | Control Group | Lovastatin ® Group | NG5006 Group |
|---|---|---|---|
| ACAT activity (pmole/min/mg protein) | 256.9 ± 39.6 | 246.1 ± 52.5 | 215.2 ± 30.3 |
| % Inhibition on ACAT Activity | 0 | 4.2 | 16.2 |

As can be seen from Table VIII, the ACAT activity observed in the NG5006-fed rat group is lower than that of the control group by 16.2%.

Example 17

Toxicity of Orally Administered NG5006

4 week-old, specific pathogen-free ICR female mice(12 heads) and male mice(12 heads) were bred under a condition of temperature 22±3° C., moisture 55±10% and photoperiod 12L/12D. Fodder(Cheiljedang Co., mouse and rat fodder) and water were sterilized and fed to the mice.

NG5006 was dissolved in 0.5% Tween 80 to a concentration of 100 mg/ml. The solution thus obtained was orally administered to the mice in amounts of 0.2 ml(1 g/kg), 0.4 ml(2 g/kg) and 0.8 ml(4g/kg) per 20 g of mouse body weight, respectively. The solution was administered once and the mice were observed for 7 days for signs of adverse effects or death according to the following schedule: 1, 4, 8, and 12 hours after the administration and, every 12 hours thereafter. The weight changes of the mice were recorded every day to examine the effect of NG5006. Further, on the 7th day, the mice were sacrificed and the internal organs were visually examined.

All the mice were alive at day 7 and NG5006 showed no toxicity. The autopsy revealed that the mice did not develop any pathological abnormality, and no weight loss was observed during the 7 day test period. Accordingly, it was concluded that NG5006 is not toxic when orally administered to an animal.

Formulation 1: Preparation of Pharmaceutical Formulation

Hard gelatin capsules were prepared using the following ingredients:

|  | Quantity (mg/capsule) |
|---|---|
| Active ingredient (NG5006) | 20 |
| Starch, dried | 160 |
| Magnesium Stearate | 20 |
| Total | 200 |

The above ingredients were mixed thoroughly and filled in a hard gelatin capsule.

Formulation 2: Foods containing flavanone derivatives

Foods containing NG5006 obtained in Example 1 were prepared as follows.

(1) Preparation of tomato ketchup and sauce 0.2 wt % of NG5006 was added to a tomato ketchup or sauce to obtain a health-improving tomato ketchup or sauce.

(2) Preparation of wheat flour foods 0.5 wt % of NG5006 was added to wheat flour and breads, cakes, cookies, crackers and noodles were prepared by using the mixture to obtain health-improving foods.

(3) Preparation of soups and gravies 0.1 wt % of NG5006 was added to soups and gravies to obtain health-improving soups and gravies.

(4) Preparation of ground beef 10 wt % of NG5006 was added to ground beef to obtain a health-improving ground beef.

(5) Preparation of dairy product 5 wt % of NG5006 was added to milk and various dairy products such as butter and ice cream were prepared by using the milk.

However, in case of cheese preparation, NG5006 was added to the coagulated milk protein; and, in case of yogurt preparation, NG5006 was added to the coagulated milk protein obtained after the fermentation.

Formulation 2: Beverages containing flavanone derivatives (1) Preparation of vegetable juice 5 g of NG5006 was added to 1000 ml of a tomato or carrot juice to obtain a health-improving vegetable juice.

(2) Preparation of fruit juice 1 g of NG5006 was added to 1000 ml of an apple or grape juice to obtain a health-improving fruit juice.

While the invention has been described with respect to the above specific embodiments, it should be recognized that various modifications and changes may be made to the invention by those skilled in the art which also fall within the scope of the invention as defined by the appended claims.

What is claimed is:

1. A compound of formula (I):

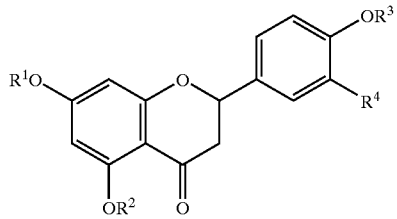

wherein,
R¹ is R⁵ R⁶CO group;
R² is H or R⁶CO group;
R³ is H, CH₃, R⁵ or R⁶CO group;
R⁴ is H, OH, OR⁵ or R⁶COO group;
R⁵ is a $C_{2-5}$ alkyl group substituted with a phenyl group optionally having one or more substituents selected from the group consisting of $C_{1-3}$ alkyl, OH, Cl and $NO_2$; a $C_{1-5}$ alkyl group substituted with a naphthyl group optionally having one or more substituents selected from the group consisting of $C_{1-3}$ alkyl, OH, Cl and $NO_2$; a $C_{10-18}$ alkyl group; or a $C_{10-18}$ alkenyl group; and
R⁶ is a $C_{10-18}$ alkenyl group; an unsubstituted aryl group other than phenyl group; or an aryl group optionally having one or more substituents selected from the group consisting of $C_{1-3}$ alkyl, OH, Cl or $NO_2$.

2. The compound of claim 1 wherein R¹ is phenethyl, cetyl, stearyl, CH₂=CH(CH₂)₉, 1-naphthalenemethyl, oleoyl, linoleoyl, o-chlorobenzoyl, p-chlorobenzoyl, o-methoxybenzoyl, p-methoxybenzoyl or 1-naphthoyl; R² is H, oleoyl, o-chlorobenzoyl, p-chlorobenzoyl, o-methoxybenzoyl, p-methoxybenzoyl or 1-naphthoyl; and R³ is H, CH₃, phenethyl, cetyl, stearyl, oleoyl, benzoyl, o-chlorobenzoyl, p-chlorobenzoyl, o-methoxybenzoyl, p-methoxybenzoyl or 1-naphthoyl; and R⁴ is H, OH or O-oleoyl.

3. A process for preparing the compound of claim 1 which comprises (a) dissolving naringenin or hesperetin in an organic solvent; (b) adding 1 to 1.5 equivalents of an alkyl halide and 1 to 3 equivalents of a base to the solution obtained in step (a); and (c) stirring the mixture obtained in step (b) at a temperature ranging from 60 to 90° C.

4. The process of claim 3 wherein the organic solvent is selected from the group consisting of dimethylformamide (DMF), dimethylsulfoxide(DMSO), tetrahydrofuran(THF), acetone and mixture thereof.

5. The process of claim 3 wherein the alkyl halide is hexadecanyl bromide or octadecanyl bromide.

6. A process for preparing the compound of claim 1 which comprises (a) dissolving naringenin or hesperetin in an organic solvent; (b) adding 1 to 10 equivalents of triethylamine(Et₃N) to the solution obtained in step (a); (c) cooling the mixture obtained in step (b); (d) adding 1 to 10 equivalents of acyl chloride to the mixture obtained in step (c); and (e) reacting the mixture obtained in step (c) for 2 to 20 hours.

7. The process of claim 6 wherein the organic solvent is tetrahydrofuran(THF) or dichloromethane(CH₂Cl₂).

8. The process of claim 6 wherein acyl chloride is selected from the group consisting of oleoyl chloride, benzoyl chloride, p-chlorobenzoyl chloride, o-chlolbenzoyl chloride, p-methoxybenzoyl chloride, o-methoxybenzoyl chloride and 1-naphthoyl chloride.

9. A pharmaceutical composition for treating or preventing an elevated blood lipid level-related disease in a mammal, which comprises an effective amount of the compound of claim 1 as an active ingredient together with a pharmaceutically acceptable carrier.

10. The composition of claim 9 wherein the disease is hyperlipidemia, arteriosclerosis, angina pectoris, stroke or fatty liver.

11. A pharmaceutical composition for inhibiting the activity of acyl-CoA:cholesterol-O-acyltransferase(ACAT) in a mammal, which comprises an effective amount of the compound of claim 1 as an active ingredient together with a pharmaceutically acceptable carrier.

12. A pharmaceutical composition for inhibiting the activity of 3-hydroxy-3-methylglutaryl CoA(HMG-CoA) reductase in a mammal, which comprises an effective amount of the compound of claim 1 as an active ingredient together with a pharmaceutically acceptable carrier.

13. A food or beverage composition for treating or preventing an elevated blood lipid level-related disease in a mammal, which comprises an effective amount of the compound of claim 1 as an active ingredient together with a pharmaceutically acceptable carrier.

14. The composition of claim 13 wherein the disease is hyperlipidemia, arteriosclerosis, angina pectoris, stroke or fatty liver.

15. A food or beverage composition for inhibiting the activity of acyl-CoA:cholesterol-O-acyltransferase(ACAT) in a mammal, which comprises an effective amount of the compound of claim 1 as an active ingredient together with a pharmaceutically acceptable carrier.

16. A food or beverage composition for inhibiting the activity of 3-hydroxy-3-methylglutaryl CoA(HMG-CoA) reductase in a mammal, which comprises an effective amount of the compound of claim 1 as an active ingredient together with a pharmaceutically acceptable carrier.

17. A method for treating or preventing an elevated blood lipid level-related disease in a mammal, which comprises administering an effective amount of the compound of claim 1 thereto.

18. The method of claim 17 wherein the disease is hyperlipidemia, arteriosclerosis, angina pectoris, stroke or fatty liver.

19. A food or beverage composition for inhibiting the activity of acyl-CoA:cholesterol-O-acyltransferase(ACAT) in a mammal, which comprises administering an effective amount of the compound of claim 1 thereto.

20. A food or beverage composition for inhibiting the activity of 3-hydroxy-3-methylglutaryl CoA(HMG-CoA) reductase in a mammal, which comprises administering an effective amount of the compound of claim 1 thereto.

* * * * *